United States Patent

Papenfuhs et al.

[11] 4,002,630
[45] Jan. 11, 1977

[54] NOVEL AROMATIC O-HYDROXYALDEHYDES, A PROCESS FOR THEIR PREPARATION AND THEIR UTILIZATION

[75] Inventors: Theodor Papenfuhs, Frankfurt am Main; Helmut Tröster, Schneidhain, Taunus, both of Germany

[73] Assignee: Hoechst Aktiengesellschaft, Frankfurt am Main, Germany

[22] Filed: July 22, 1975

[21] Appl. No.: 598,070

[30] Foreign Application Priority Data

July 26, 1974 Germany .................... 2436032

[52] U.S. Cl. .............. 260/281 Q; 260/251 Q; 260/281 N; 260/281 NH; 260/281 S; 260/343.5; 260/247.2 A; 260/520 D; 260/282; 260/268 TR; 106/288 Q; 252/301.26; 424/267
[51] Int. Cl.² ............................ C07D 217/24
[58] Field of Search ..... 260/281 A, 281 NH, 281 N

[56] References Cited

OTHER PUBLICATIONS

Karpukhin et al., Chem. Abs. 71, 30275b (1969).

*Primary Examiner*—Alton B. Rollins
*Assistant Examiner*—Mark L. Berch
*Attorney, Agent, or Firm*—Connolly and Hutz

[57] ABSTRACT

Novel aromatic o-hydro-aldehydes of the formula

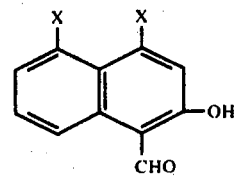

(I)

have been found wherein each X is a carboxy group or both X together are a group of the formula

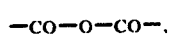

or

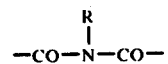

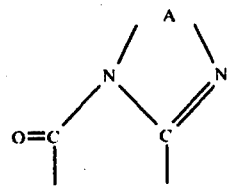

wherein R stands for hydrogen, an optionally substituted amino group, optionally etherified hydroxy group, an optionally substituted aliphatic, cycloaliphatic, aromatic or heterocyclic radical, and A for an optionally substituted phenylene or naphthylene radical. They are valuable intermediate products for the preparation of dyestuffs, optical brighteners, textile auxiliaries and pharmaceutica and are particularly suitable for the preparation of azo-methine dyestuffs which are obtained by condensation of these aldehydes with suitable amines.

5 Claims, No Drawings

NOVEL AROMATIC O-HYDROXYALDEHYDES, A PROCESS FOR THEIR PREPARATION AND THEIR UTILIZATION

The present invention concerns novel aromatic o-hydroxyaldehydes of the formula (I)

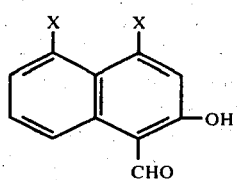

(I)

in which each X represents a carboxylic acid group or both together a group of the formula

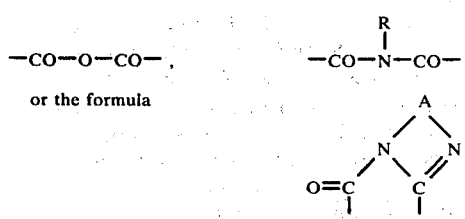

or the formula wherein R stands for hydrogen, an optionally substituted amino group, optionally etherified hydroxy group, an optionally substituted aliphatic, cycloaliphatic, aromatic or heterocyclic radical, and A for an optionally substituted phenylene or naphthylene radical.

The invention concerns therefore as novel compounds the 4,5-dicarboxy-2-hydroxy-naphthaldehyde of the formula (II), its anhydride of the formula (III), its imide compounds of the formula (IV) and the naphthoylene arylimidazole, respectively naphthoylene, pyrimidine derivatives of the formula (V), in which R and A have the beforementioned signification.

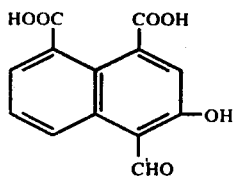

(II)

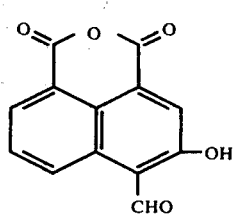

(III)

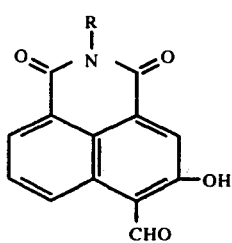

(IV)

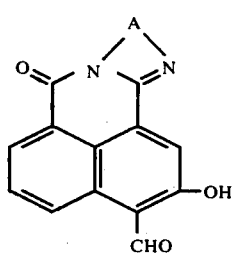

(V)

The dicarboxylic acid compound of the formula (II) can also be used in the form of its salts, for example, as alkaline, alkaline earth metal or ammonium salt. Preference is given to the compounds of the formulae (IV) and (V).

The novel aromatic o-hydroxyaldehydes of the invention can be obtained according to the invention by reaction of compounds of the formula (VI)

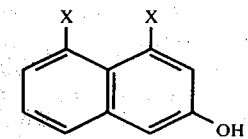

(VI)

in which both X have the abovementioned significations, in presence of a lower, optionally halogen-substituted mono- or dicarboxylic acid, with hexamethylenetetramine. The process is advantageously effected in the following way: the starting compound of the formula (VI) is dissolved or suspended, in general, in an aliphatic carboxylic acid of two to 10 times of the quantity of the starting compound and heated for a longer time at temperatures up to 120° C, preferably up to 80° – 100° C, whereby it is necessary to add, except in the case of trifluoroacetic acid, a small quantity of a mineral acid such as sulfuric acid or hydrochloric acid. The acid can be added in mixture with the carboxylic acid either directly or afterwards. Especially suitable for the reaction as lower carboxylic acids are acetic acid but also propionic acid, lactic acid, valeric acid, furthermore dicarboxylic acids such as, adipinic acid or malonic acid, or halogeno-fatty acids such as chloro acetic acid, trichloro-acetic acid or trifluoro acetic acid. Hexamethylenetetramine can also be replaced by a mixture of ammonia and formaldehyde, effecting in the same way. Ammonia and formaldehyde can be used in the form of an aqueous solution or as gas.

Hexamethylenetetramine is used in stoichiometric quantities or in quantities somewhat in excess. In addition to that it is possible to use paraformaldehyde with a mol-ratio of 1 : 1 to 3 : 1, related to the starting compound of the formula (VI).

The compounds of the invention corresponding to the formulae (IV) and (V) can also be obtained by reaction of the novel aldehydes of the formulae (II) and (III), preferably of (III), with amino compounds of the formula H₂N—R or H₂N—A—NH₂, in which R and A have the beforementioned signification, whereby the second amino group stands in ortho- or peri-position in respect of the first one, this means with ammonia, hydrazines, optionally etherified hydroxylamines, primary aliphatic cycloaliphatic, aromatic or heterocyclic amines or aromatic ortho- or peri-diamines whereby normally Schiff's bases are formed in an intermediate stage, deriving from the compounds (IV) and (V) as well as from amino compounds used; afterwards these bases can easily be converted into the free hydroxyaldehydes with the aid of an acid or basic hydrolysis. Compounds of the formulae (IV) or (V) can also be obtained in an especially advantageous way by an one-pot reaction from 3-hydroxynaphthalic acid (IV, X = COOH) or its anhydride by condensing them in a suitable solvent for the aldehyde synthesis of the invention with stoichiometric quantities of an amine or o-diamine for several hours at about 80° – 120° C; subsequently, the condensation products are reacted without isolation by addition of hexamethylenetetramine and eventually paraformaldehyde and/or mineral acid to the aldehydes of the formulae (IV) or (V).

As hydrazines of the formula $H_2N$—R there can be cited, beside the hydrazine itself, the N-alkyl-, N-aralkyl- or N-aryl-hydrazines as well as hydrazine compounds containing a heterocyclic radical, for example, N-methyl-, N-($\beta$-hydroxyethyl)-, N-benzyl-, phenyl- or naphthylhydrazine, whereby their aromatic nuclei may contain substituents such as alkyl, alkoxy, alkylalkoxy, trifluoro-methyl groups or halogen atoms, furthermore N-aminomorpholine or N-aminopiperidine as well as 2-hydrazinobenzthiazole, 2-hydrazinopyridine or 2-hydrazinoquinoline. Out of the radicals mentioned above, containing alkyl or alkylene radicals, those are preferred containing 1 to 4 C-atoms in each alkyl or alkylene moiety.

As aliphatic radicals R, those of straight-chained or ramified amines carrying 1 – 18 carbon atoms, especially 1 – 7 carbon atoms, can be mentioned, furthermore those, which are substituted by halogen atoms, such as fluorine, chlorine or bromine atoms, by alkoxy groups of 1 to 6 C-atoms, such as methoxy, ethoxy, propoxy or butoxy groups, by hydroxy, amino, carboxylic acid, carboxylic acid amide or nitrile groups or by an aryl radical, for example, by a phenyl or naphthyl radical, or by a saturated, unsaturated or aromatic heterocyclic radical, for example, a pyridine, morpholine, pyrazole, imidazole, triazole, thiazole, thiodiazole pyrimidine, furane, piperazine or azabicyclononane radical. As cyclo-aliphatic radicals R there can, for example, be cited those of such amines, which contain the cyclopentyl, cyclohexyl, alkylcyclohexyl or halogenocyclohexyl radical. As aromatic radicals R there can be cited particularly those which derive from aniline or from a naphthylamine, whereby their aromatic nuclei can contain as substituents preferably halogen atoms such as chlorine or bromine, alkyl groups with 1 – 4 carbon atoms, alkoxy groups with 1 – 4 carbon atoms, hydroxy or nitro-groups, sulfonamide, carbonamide, acylamino groups of aliphatic or aromatic carboxylic acids, such as acetylamino, propionylamino or benzoylamino, and/or cyano groups. Therefrom can be mentioned, beside aniline, the chloranilines, toluidines, xylidines, anisidines, phenetidines, nitroanilines, chloroansidines, dimethoxy-anilines, chloro-dimethoxyanilines, methoxymethylanilines, 1- and 2-aminonaphthaline and its chloro-substituted derivatives.

As heterocyclic radicals R there can especially be cited those with a 5- or 6-membered, nitrogen containing radical such as, for example, the pyridine, pyrazole, imidazole, triazole, oxazole, thiazole, thiadiazole or pyrimidine radical, or their substitution-products as well as their oxo and/or benzo compounds, whereby the benzene radicals may contain halogen atoms such as fluorine, chlorine or bromine atoms, alkyl groups, particularly those with 1 – 4 carbon atoms, alkoxy groups, particularly those with 1 – 4 carbon atoms, nitro, trifluoromethyl, nitrile, carbonamide and or alkylsulfonyl groups, especially of 1 to 4 C-atoms.

The arylene radical A may be an ortho-phenylene radical or an ortho- or perinaphthylene radical, which may be substituted by halogen atoms such as chlorine or bromine atoms, lower alkyl groups such as methyl, ethyl or propyl groups, hydroxy or aryloxy groups such as optionally substituted phenoxy groups, aralkoxy groups such as benzyloxy groups, nitrile, trifluoromethyl, carboxylic acid alkyl ester or carboxylic acid aralkyl ester or carboxylic acid amide groups, preferably containing alkyl or alkylene radicals of 1 to 5 C-atoms.

The starting compounds of the formula (VI) which are partially known, can be obtained with known methods according to the following scheme:

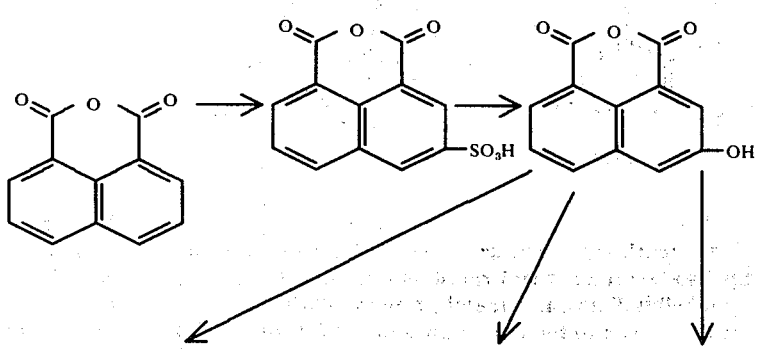

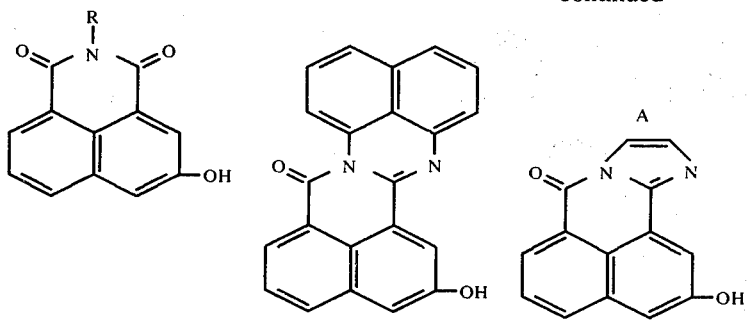

Their preparation is described, for example, in "Chemische Berichte," Vol, 32 (1889), p. 3283, "Helvetica Chimica Acta," Vol. 33 (1950), p. 530, "Deutsche Auslegeschrift" No. 1.048.374 and in the Russian Pat. No. 259.892.

The aromatic o-hydroxyaldehydes of the invention are valuable intermediate products for the preparation of dyestuffs, optical brighteners, textile auxiliaries and pharmaceutica. They are particularly suitable for the preparation of azomethine dyestuffs which are obtained by condensation of these aldehydes with suitable amines.

Especially advantageous are the compounds of the formulae (IV) and (V), in which R stands for an alkyl radical with 1 – 4 carbon atoms which may be substituted by hydroxy or alkoxy groups with 1 – 4 carbon atoms, or which stands for a phenyl- or naphthyl radical, which may be substituted by carbonamide groups or cyclic carbonamide groups, by alkoxy groups of 1 to 4 carbon atoms or halogen atoms, such as chlorine or bromine, or for a triazolyl or benzthiazolyl or benzimidazolyl radical and A represents an o-phenylene-, o-naphthylene or peri-naphthylene radical, which may also be substituted by carbonamide or cyclic amide groups, alkoxy groups with 1 – 4 carbon atoms or by halogen atoms such as chlorine or bromine.

Beside the compounds of the above formula (IV), in which R stands for an alkyl radical with 1 – 4 carbon atoms which may be substituted by hydroxy or alkoxy groups with 1 – 4 carbon atoms, preference is given to those, which have as radical R the cyclopentyl, cyclohexyl, benzyl or phenethyl radical.

The following examples illustrate the invention. Parts are parts by weight.

EXAMPLE 1

21.4 parts of 3-hydroxynaphthalic acid anhydride, 21.0 parts of hexamethylenetetramine and 4.5 parts of paraformaldehyde were put into 300 parts of glacial acetic acid. The mixture was heated during 6 hours at 100° C. 80 parts of concentrated hydrochloric acid were then added, and stirring was continued for 2 hours at 100° C. The reaction mixture was cooled to 40° C, and 400 parts of water were added; the resulting precipitate was suction-filtered, washed until neutral and dried. 18.4 parts (76.0 % of the theory) of aldehyde, corresponding to the formula

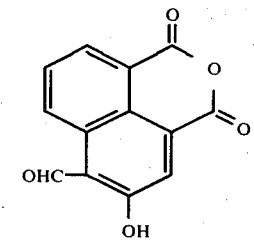

were obtained; recrystallized from acetic acid, clear yellow crystals with a melting point of 211° C result.

EXAMPLE 2

28.6 parts of a mixture of hydroxy naphthoylene benzimidazole isomers having the formulae

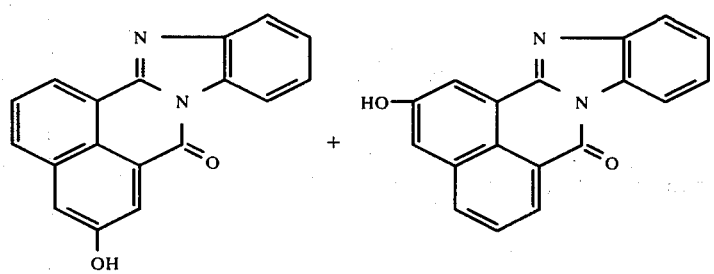

obtained by reaction of 3-hydroxynaphthalic acid anhydride with the stoichiometric amount of o-phenylenediamine in water at 120° C, 14.0 parts of hexamethylenetetramine and 3.0 parts of paraformaldehyde, were heated in 250 parts of a 85 % by weight monochloro acetic acid for 4 hours at 90° C. 80 parts of a 50 % b.w. sulfuric acid were then added, and the whole was heated at 100° C for 1 hour.

The mixture of the reaction was then stirred at room temperature into 2000 parts of water; the so obtained suspension was filtered, the filter residue was washed until neutral and dried. 28.4 parts (90.4 % of the theory) of an aldehyde mixture of the formulae

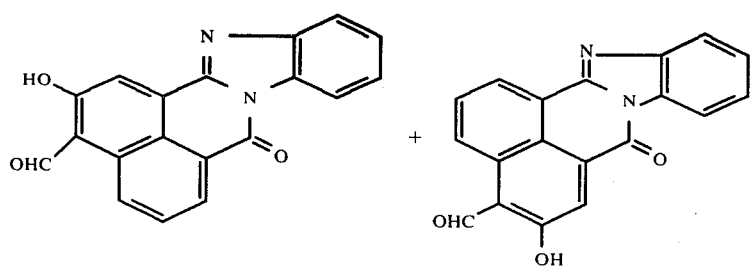

were obtained: orange crystals,
melting point (from acetic acid): 332–335° C

When an equivalent amount of a 37 % b.w. hydrochloric acid was used instead of a 50 % sulfuric acid, the same compounds as mentioned above were obtained with practically the same yield.

EXAMPLE 3

21.4 parts of 3-hydroxynaphthalic acid anhydride were suspended in 300 parts of glacial acetic acid; 9.0 parts of methoxypropylamine were added dropwise, and the mixture was then boiled under reflux during 8 hours. After cooling it to 80° C, 14.0 parts of hexamethylene-tetramine and 3.0 parts of paraformaldehyde were added, and the whole was stirred during 5 hours at 80° C. After addition of 90.0 parts of a 30 % b.w. hydrochloric acid and further stirring for 2 hours at 80° C, the reaction mixture was put into 1750 parts of water. The precipitated product was suction-filtered, washed until neutral and dried. 22.2 parts (71 % of the theory) of an aldehyde were obtained which corresponds to the formula

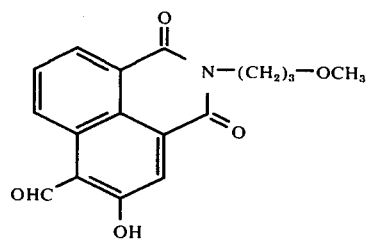

Clear yellow crystals,
melting point (glacial acetic acid): 146° C.

EXAMPLE 4

17.3 parts of 3-hydroxynaphthalic acid-5'-benzimidazolonylimide of the formula

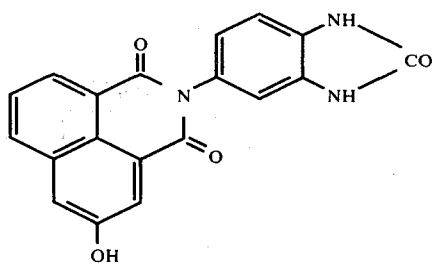

(prepared by reaction of 3-hydroxynaphthalic acid anhydride with stoechiometric amounts of 5-aminobenzimidazolone in N-methylpyrrolidone at 120°C)

were put slowly, together with 10.5 parts of hexamethylenetetramine and 2.2 parts of paraformaldehyde, into 200.0 parts of trifluoro acetic acid and were heated. A solution was obtained at 80° C. Subsequently the mixture was heated up to 105° C, and this temperature was kept for 90 minutes. The hot reaction mixture was then poured into 1000 parts of water, the precipitate was suction-filtered, washed until neutral and dried. 16.8 parts (90 % of the theory) of aldehyde were obtained, corresponding to the formula

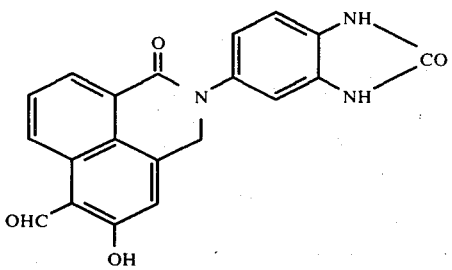

Colorless crystals,
Melting point (trichloro acetic acid): >345° C

EXAMPLE 5

227.0 parts of 3-hydroxynaphthalic acid-N-methylimide, prepared by condensation of 3-hydroxynaphthalic acid anhydride with stoichiometric amounts of monomethylamine in water at 120° C, 140.0 parts of hexa-methylenetetramine and 30.0 parts of paraformaldehyde were successively introduced into 3000 parts of glacial acetic acid; the mixture was stirred for 5 hours at 100° C.

150.0 parts of a 95 % sulfuric acid diluted with 90.0 parts of water, were added dropwise within 30 minutes. The reaction mixture was stirred for 1 hour, and subsequently 150.0 parts of a 95 % b.w. sulfuric acid were added, whereby a clear solution was obtained. The reaction was brought to an end while stirring for 1 hours at 100° C. The solution resulting from the reaction was cooled to 20° C, the precipitate was separated by filtration, washed with water until neutral and dried.

200.0 parts (88.8 % of the theory) of aldehyde were obtained, corresponding to the formula

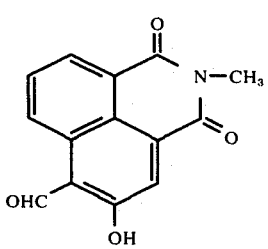

clear yellow crystals,
melting point (glacial acetic
acid): 235° C

EXAMPLE 6

24.2 parts of hydroxynaphthalic acid anhydride-4-aldehyde, prepared according to example 1, were suspended in 350.0 parts of water. 10.0 parts of glacial acetic acid as well as 32.0 parts of 1,8-diamino-naphthalene were added. The mixture was then heated in the autoclave under stirring during 8 hours at 110° C. Subsequently, 45.0 parts of a 95 % b.w. sulfuric acid were added, and stirring was continued for 2 hours at 110° C. After cooling and release, the product was filtered, washed until neutral and dried. 35.1 parts (96.4 % of the theory) of an aldehyde mixture were obtained, corresponding to the formulae

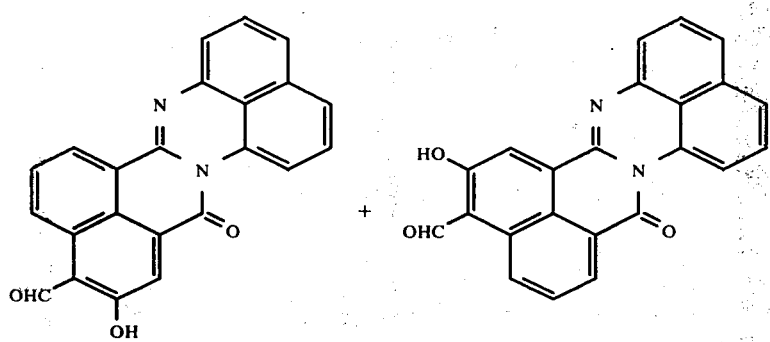

After recrystallization from dimethylformamide, red crystals with a melting point of above 345° C were obtained.

EXAMPLE 7

21.3 parts of 3-hydroxynaphthalimide, 27.2 parts of a 25 % b.w. aqueous ammonia, 12.0 parts of a 40 % b.w. aqueous solution of formaldehyde and 300.0 parts of glacial acetic acid were heated for 5 hours at 100° C. Afterwards, 80.0 parts of a 30 % by weight hydrochloric acid were added. Stirring was continued during 2 hours at 100° C, and the reaction mixture was then pured into 500.0 parts of water; the precipitate was separated by filtration, washed until neutral and dried. 15.6 parts (64.9 % of the theory) of the aldehyde corresponding to the formula

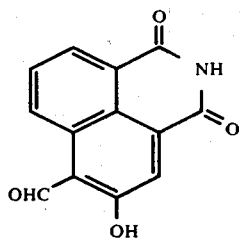

Yellow crystals,
Melting point (glacial acetic
acid): 294° C.

EXAMPLE 8

28.0 parts of 3-hydroxynaphthalic acid-triazolylimide of the formula

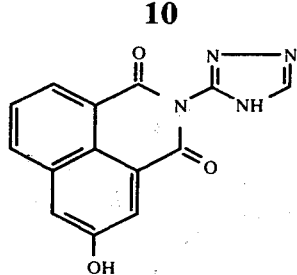

(prepared by reaction of equimolar
amounts of 3-oxynaphthalic acid
anhydride and 3-aminotriazole-
(1,2,4) in glacial acetic acid at
105°C)

14.0 parts of hexamethylenetetramine, 3.0 parts of paraformaldehyde and 180.0 parts of propionic acid were stirred for 3 hours at 90° C.

Then, 70.0 parts of concentrated hydrochloric acid were added, stirring was continued at 95° C for 100 minutes; the reaction mixture was then poured into 2000 parts of water, the precipitate was separated by filtration, washed until neutral and dried. 28.0 Parts (90.9 % of the theory) of aldehyde were obtained, corresponding to the formula

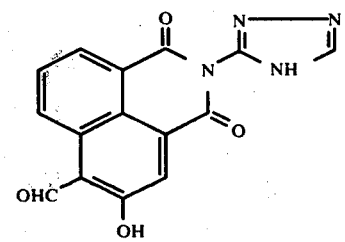

Clear yellow crystals,
Melting point (glacial acetic
acid): 315° C.

EXAMPLES 9 – 15

When the methoxypropylamine in Example 3 was replaced by corresponding amounts of an amine of the formula $R-NH_2$, indicated in Table 1, and the reaction process was carried out in the same way, novel aldehydes according to the general formula

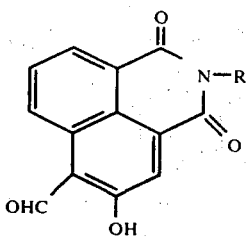

were obtained; they are listed in the following table, showing yield and melting point.

TABLE 1

| Ex. | R | Yield in % | Melting point °C |
|---|---|---|---|
| 9 | —$C_2H_5$ | 74.3 | 189 |
| 10 | —$(CH_2)_3$—$CH_3$ | 69.8 | 136 |
| 11 |  | 78.8 | 247 |
| 12 | | 73.0 | 287 |
| 13 | | 81.5 | >345 |
| 14 | | 83.2 | >345 |
| 15 | | 71.8 | 291 |
| 15a | | 67 | 161 |

TABLE 1-continued

| Ex. | R | Yield in % | Melting point °C |
|---|---|---|---|
| 15b | —$CH_2CH_2OH$ | 64 | 182 |

EXAMPLE 16 – 21

When the methoxypropylamine of Example 3 was replaced by corresponding amounts of o- or peri-diamines, as shown in Table 2, of the formulae;

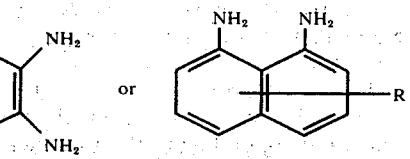

and the reaction is carried out in the same way, aldehyde mixtures, as shown in Table 2, according to the general formulae

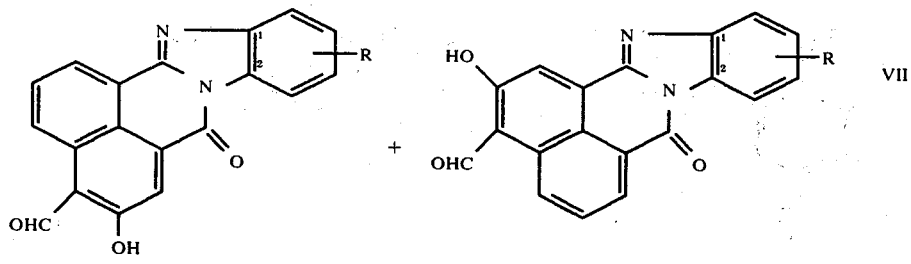 VII or

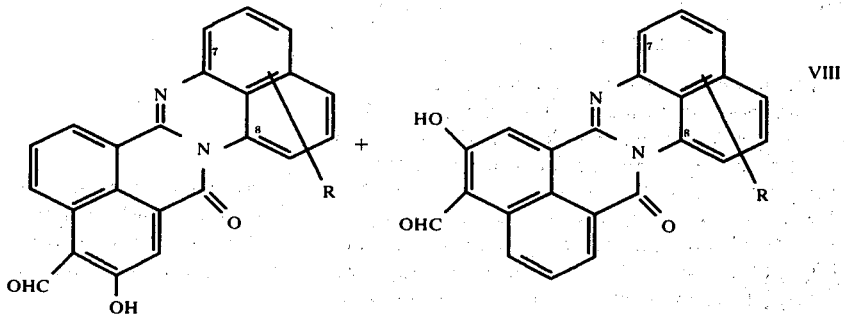 VIII were obtained with the yields and melting points indicated in Table 2.

TABLE 2

| Ex. | R | Formula | Yield in % | Melting point °C |
|---|---|---|---|---|
| 16 | 4-$OCH_3$ | VII | 67.9 | 337 |
| 17 | 4-CN | VII | 73.8 | >345 |
| 18 | 3-Cl | VII | 65.8 | >345 |
| 19 | 4-$CH_3$ | VII | 71.6 | 329 |
| 20 | 4-Cl | VIII | 89.6 | >345 |
| 21 | 6-$SO_2CH_3$ | VIII | 92.4 | >345 |

EXAMPLES 22 – 29

When the 1,8-diaminonaphthaline of example 6 was replaced by corresponding amounts of an amine of the formula R—$NH_2$ as listed in Table 3, and the reaction izs carried out in the same way, aldehydes of the invention, corresponding to the general formula

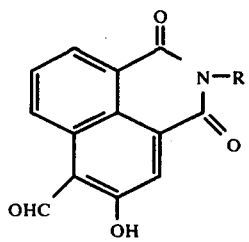

shown in Table 3 were obtained with the yields and melting points indicated therein.

TABLE 3

| Ex. | R | Yield in % | Melting point °C |
|---|---|---|---|
| 22 | —NH$_2$ | 77.0 | >345 |
| 23 | —NH—C$_6$H$_5$ | 74.3 | >345 |
| 24 | cyclopropyl-CH(CH$_3$)— | 61.7 | 189 |
| 25 | imidazolyl | 79.2 | >345 |

TABLE 3-continued

| Ex. | R | Yield in % | Melting point °C |
|---|---|---|---|
| 26 | (methyl, Cl-substituted phenyl with NH–CO–NH) | 91.0 | >345 |
| 27 | —(CH$_2$)$_2$—C$_6$H$_5$ | 65.8 | 197 |
| 28 | —(CH$_2$)$_3$—OC$_4$H$_9$ | 70.8 | 154 |
| 29 | —OH | 64.4 | >345 |

EXAMPLES 30 – 37

When 3-hydroxynaphthalic acid methylimide, as used in Example 5, was replaced by equivalent amounts of 3-hydroxynaphthalic acid derivatives as shown in Table 4, and the reaction is carried out in the usual way, corresponding aldehydes or aldehyde mixtures were obtained with the yields and melting points indicated. The starting products, shown in Table 4, were synthesized in analogy to known processes by reaction of equimolar amounts of 3-hydroxynaphthalic acid anhydride with the corresponding amino compounds in glacial acetic acid.

TABLE 4

| Ex. | Starting Product | Yield in % | Melting point °C |
|---|---|---|---|
| 30 | (structure with H$_3$CO, CONH–phenyl, OH) | 88.8 | >345 |
| 31 | (structure with 2,4-dimethylphenyl, OH) | 70.8 | 292 |
| 32 | (structure with 3,5-bis-COOC$_2$H$_5$-phenyl, OH) | 79.3 | 241 |

TABLE 4-continued

| Ex. | Starting Product | Yield in % | Melting point °C |
|---|---|---|---|
| 33 | | 85.0 | >345 |
| 34 | | 81.4 | >345 |
| 35 | | 65.3 | 198 |
| 36 | (+ isomers) | 92.8 | >345 |
| 37 | (+ isomers) | 83.7 | >345 |

We claim:
1. A compound of the formula

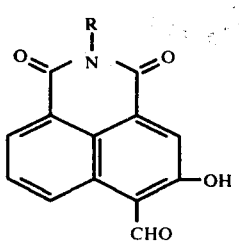

in which R is alkyl of 1 – 4 carbon atoms, or alkyl of 1 to 4 carbon atoms substituted by hydroxy or alkoxy of 1 to 4 carbon atoms, or is cyclopentyl, cyclohexyl, benzyl or phenethyl.

2. The compound according to claim 1, in which R is methyl.

3. The compound according to claim 1, in which R is ethyl.

4. The compound according to claim 1, in which R is $CH_3O$–$(CH_2)_3$- (=γ-methoxy-n-propyl).

5. The compound according to claim 1, in which R is cyclohexyl.

* * * * *